United States Patent [19]

Ayasse

[11] Patent Number: 5,344,849
[45] Date of Patent: Sep. 6, 1994

[54] CATALYTIC PROCESS FOR THE PRODUCTION OF HYDROCARBONS

[75] Inventor: Conrad Ayasse, Calgary, Canada

[73] Assignee: Canada Chemical Corporation, Calgary, Canada

[21] Appl. No.: 966,953

[22] Filed: Oct. 27, 1992

Related U.S. Application Data

[63] Continuation-in-part of Ser. No. 795,153, Nov. 20, 1991, abandoned, which is a continuation of Ser. No. 606,755, Oct. 31, 1990, abandoned.

[51] Int. Cl.$^5$ .............................. C07L 1/04
[52] U.S. Cl. .............................. 518/713; 518/714; 518/721
[58] Field of Search .............. 518/713, 714, 721

[56] References Cited

U.S. PATENT DOCUMENTS 4,096,163  6/1978  Chang et al. .................. 518/713
4,338,089  7/1982  Shaper et al. .................. 518/713

FOREIGN PATENT DOCUMENTS 1111073  10/1981  Canada .
1111074  10/1981  Canada .
1204099   5/1986  Canada .
2006260   3/1979  United Kingdom .

*Primary Examiner*—Howard T. Mars
*Attorney, Agent, or Firm*—Millen, White, Zelano & Branigan

[57] ABSTRACT

Single-stage catalytic conversion of a gas mixture, having a molar ratio of hydrogen to carbon monoxide greater than 1.9, to hydrocarbons boiling in the gasoline or diesel range, is achieved using three catalysts in admixture. The first is a Fischer-Tropsch catalyst with catalytic activity for the conversion of $H_2$ and CO into hydrocarbons. The second is a methanol conversion catalyst with catalytic activity for the conversion of methanol into hydrocarbons, such as a crystalline aluminosilicate zeolite or crystalline silicate. Finally, the third is a methanol synthesis catalyst with catalytic activity for both the water-gas shift reaction and methanol synthesis. This combination of catalysts provides high carbon conversion of CO to hydrocarbons, and a high yield of liquid products.

13 Claims, 3 Drawing Sheets

CATALYTIC PROCESS FOR THE PRODUCTION OF HYDROCARBONS

CROSS-REFERENCE TO RELATED APPLICATIONS

This application is a continuation-in-part of application Ser. No. 07/795,153 filed Nov. 20, 1991 which is a continuation application of application Ser. No. 07/606,755, filed Oct. 31, 1990 both now abandoned.

FIELD OF THE INVENTION

The present invention relates to a catalytic process for the production of hydrocarbons from hydrogen and carbon monoxide.

BACKGROUND OF THE INVENTION

Applicant sought a method for the once-through direct single stage conversion of synthesis or reformer gas to high quality synthetic fuel, to achieve a high yield of hydrocarbons, i.e. a high carbon conversion from CO to hydrocarbons. Synthesis gas has a highly variable $H_2$ to CO molar ratio of about 2. Synthesis gas from coke or coal generally, has a low $H_2$ to CO ratio, generally less than about 1.0. Synthesis gas from methane typically has a $H_2/CO$ ratio greater than 1.9, usually in the range of 2.0–3.0. Reformer gas typically has a $H_2$ to CO molar ratio of about 3.

Dwyer et al U.S. Pat. No. 4,172,843 discloses a process for single stage catalytic conversion of synthesis gas to hydrocarbon mixtures. This process makes use of two catalysts. The catalysts used are a Fischer-Tropsch catalyst and a methanol conversion catalyst. Dwyer attained a 33% yield using this method.

Fischer-Tropsch catalysts contain one or more metal components from Group VIII of the periodic Table, such as iron, cobalt, nickel, rhodium and ruthenium. Typical Fischer-Tropsch catalysts are potassium promoted fused iron oxide catalysts. These have activity for the conversion of hydrogen and carbon monoxide or carbon dioxide to hydrocarbons, according to the following reactions:

$$CO + 2H_2 \rightarrow (-CH_2-) + H_2O$$

$$CO_2 + 3H_2 \rightarrow (-CH_2-) + 2H_2O.$$

However, the product yielded by a Fischer-Tropsch catalyst alone includes a mixture of carbon dioxide, water, alcohols, and hydrocarbons, due to a number of side reactions, more specifically:

the water-gas shift reaction:

$$CO + H_2O \rightleftharpoons CO_2 + H_2$$

the methanol synthesis reaction:

$$CO + 2H_2 \rightleftharpoons CH_3OH$$

and the formation of methane, by a number of reactions:

$$CO + 3H_2 \rightarrow CH_4 + H_2O$$

$$2CO + 2H_2 \rightarrow CH_4 + CO_2$$

$$CO_2 + 4H_2 \rightarrow CH_4 + 2H_2O.$$

Also, the hydrocarbons produced by a Fischer-Tropsch catalyst alone are of poor quality, containing waxy paraffins which are unsuitable for use in gasoline.

The water-gas shift (WGS) side reaction is of particular significance, since it can lead to high carbon losses, due to the formation of $CO_2$. This is a reversible exothermic reaction-low temperatures (less than 350° C.) favour forward CO conversion to $CO_2$, whereas higher temperatures favour the reverse. The water-gas shift reaction changes the oxygen-containing by-products from $H_2O$ to $CO_2$, and alters the usage ratio of hydrogen and carbon monoxide in the Fischer-Tropsch synthesis. It has also been shown to occur in parallel with the methanol synthesis reaction starting with $CO_2$ (Amenomiya, Y. *Applied Catalysis*, 30, 57-68, 1987).

Dwyer found that if a Fischer-Tropsch catalyst was combined with a methanol conversion catalyst, a better quality product was obtained.

A methanol conversion catalyst, such as crystalline zeolite, has activity for the conversion of methanol into hydrocarbons, according to the following reaction:

$$2CH_3OH \longrightarrow CH_3OCH_3 \longrightarrow C_2\text{-}C_5 \longrightarrow \begin{array}{l}\text{paraffins}\\\text{aromatics}\\\text{cycloparaffins}\\C_6^+ \text{ olefins.}\end{array}$$

Dwyer's combination of a Fischer-Tropsch catalyst and a crystalline zeolite gives a high quality hydrocarbon product. However, there is poor conversion of carbon and a poor yield of 33%. Further, because of the exothermicity of both the Fischer-Tropsch and methanol conversion reactions, Dwyer used a diluent to control and dissipate the heat. The diluent took up half the reaction space and so was not economical.

Another process in the prior art involved combining a methanol conversion catalyst, as described above, with a methanol synthesis catalyst. For example, see Nara, A. et al, *Mitsubishi Heavy Industries Ltd. Technical Review* Vol. 24 No. 1 (February 1987).

A methanol synthesis catalyst contains one or more metal components with activity for the conversion of hydrogen and carbon monoxide or carbon dioxide into methanol, according to the following reactions:

$$CO + 2H_2 \rightleftharpoons CH_3OH$$

$$CO_2 + 3H_2 \rightleftharpoons CH_3OH + H_2O.$$

Typical examples of a methanol synthesis catalysts include $Cu/ZnO/Cr_2O_3$ and $Cu/ZnO/Al_2O_3$.

However, methanol synthesis catalysts also are good water-gas shift reaction catalysts.

The combination of methanol synthesis and methanol conversion catalysts produces hydrocarbons according to the following:

$$2H_2 + CO \rightleftharpoons CH_3OH \rightarrow [-CH_2-] + H_2O.$$

However, the useful product yield is low. Large amounts of methane are formed, and carbon is lost to $CO_2$ due to the water-gas shift reaction.

It should be noted that Dwyer's process of Fischer-Tropsch plus methanol conversion catalysts is favoured by temperatures of 250° to 350° C. Conversely, the combination of methanol synthesis and methanol conversion catalysts is favoured by temperatures greater than 350° C. As these two catalyst combinations are effective at different temperature ranges, it would be expected that they would be incompatible. Further, as the conversion of CO to $CO_2$ by the water-gas shift reaction as promoted by the methanol synthesis catalyst is favoured at temperatures less than 350° C., it would be expected that if these two systems were combined at the lower temperature, the losses to $CO_2$ would increase in the presence of the methanol synthesis catalyst. Thus it would be expected that if the two systems were combined, carbon losses would be severe. This result is illustrated by Canadian Patents 1,111,073 and 1,111,074 issued to Shell Canada Limited.

The Shell patents were based on a feedstock from the gasification of coal, which yields a $H_2$/CO molar ratio of about 0.5. The claims in Shell were specifically limited to feedstock with $H_2$/CO less than 1.

In the Shell patents, conversion of the $H_2$ and CO to hydrocarbons using the combination of a Fischer-Tropsch catalyst plus a methanol conversion catalyst was desired. However, this combination produces hydrocarbons, as noted above, according to the following reaction:

$$2H_2 + CO \rightleftharpoons CH_3OH \rightarrow [-CH_2-] + H_2O.$$

This requires a $H_2$/CO molar ratio of 2. Thus the Shell system was deficient in hydrogen. To overcome this problem a methanol synthesis catalyst was added and the feedstream was modified to include water in order to produce hydrogen according to the water gas shift reaction. In addition to producing the needed $H_2$, this of course led to very high carbon losses to $CO_2$. Shell taught utilization of the methanol synthesis catalyst only to the extent necessary to produce $H_2$ for the hydrocarbon synthesis, as any further production would just increase carbon losses to no purpose. Therefore, it follows from the Shell teachings that a methanol synthesis catalyst should not be used in a system where hydrogen is not deficient.

This point is made by Anderson in his review paper (Anderson, J. R., Methane to Higher Hydrocarbons, Applied Catalysis, 47, p. 183, 1989):

"The formation of $H_2$ as a primary reaction product means that the possibility exists for the water-gas shift reaction in the reactor. Thus catalysts (e.g. iron) with good activity for the water-gas shift will tend to generate $CO_2$ rather than water, and simultaneously remove CO and generate $H_2$. This is a desirable situation when, as with coal-derived synthesis gas, the initial $H_2$/CO ratio is low".

SUMMARY OF THE INVENTION

Applicant analyzed the prior art and sought a method to improve on the low hydrocarbon yield obtained from the Dwyer process, which uses Fischer-Tropsch plus methanol conversion catalysts. It should be noted that both Dwyer and Applicant utilize a feedstock which is not deficient in hydrogen.

In the development of the invention, Applicant added a methanol synthesis catalyst to the Dwyer system, contrary to the teachings of the prior art. Applicant based this addition on his theory of how this catalyst would work in combination with the others. This theory contended:

that under conditions of $H_2$/CO molar ratio greater than about 1.9, the reverse water-gas shift reaction will predominate, so carbon losses to $CO_2$ will be reduced;

that the endothermic nature of the reverse water-gas shift reaction will help dissipate the heat from the exothermic reactions assisted by the Fischer-Tropsch and methanol conversion catalysts, thus making use of diluent unnecessary;

that the formation of methanol by the methanol synthesis catalyst will help the reactions of the other two catalysts along, and absorb heat;

some $CO_2$ formed by these Fischer Tropsch catalyst will be removed by reaction with hydrogen over the methanol synthesis catalyst; and that due to these factors, the yield of useful liquid hydrocarbons will improve.

When tested, Applicant found that this combination of three catalysts in admixture in one bed at one temperature was indeed effective, when applied to a feedstock having a $H_2$/CO molar ratio greater than about 1.9. Improved yields of hydrocarbons were efficiently obtained.

Therefore, according to the present invention, a gas mixture feedstock containing a $H_2$/CO molar ratio greater than 1.9 is reacted in the presence of three catalysts in admixture: Fischer-Tropsch, methanol conversion, and methanol synthesis catalysts. Preferably, the $H_2$/CO ratio ranges from 2.0 to 2.5; more preferably, from 1.9 to 2.1.

The temperature at which the process may be carried out preferably will fall in the range from 220° to 360° C. However, temperatures from 200° to 400° C. are also contemplated.

Elevated pressure at conventional levels is desirable to increase the efficiency of the reactions. The process may be carried at pressures falling in the range from 100 psig to 1000 psig, however pressures from 50 psig to 2000 psig are also contemplated.

This process has surprisingly been shown to be effective in producing a high quality hydrocarbon product boiling in the gasoline range when conducted at higher than normal pressures (greater than 200 psig and preferably greater than about 500 psig) and lower than normal temperatures (less than 240° C.). Recently, high pressure natural gas-steam reforming processes have been demonstrated. For instance, ICI has developed the LCM (Leading Concept Methanol Process) to produce synthesis gas at 600 psig or higher. Thus, the process of this invention can be operated from such LCM reactor without an intermediate gas comparison step to realize energy savings from heat losses and compression costs.

Each of the three components of the catalyst mixture are well known in the art. The Fischer-Tropsch catalyst used is preferably a promoted fused iron oxide (preferably potassium promoted). The methanol conversion catalyst is preferably either a crystalline aluminosilicate zeolite, or a crystalline silicate. The methanol synthesis catalyst is preferably an oxide of one or more of zinc, copper, iron, chromium and aluminum and may be free of, or may contain promoters.

It is contemplated that the three catalysts may be provided in different ratios, in order to adjust the composition of the product. For example, if a higher paraffin content is desired, the relative proportion of the Fischer-Tropsch catalyst should be increased. Conversely, if a higher aromatic content is desired, the relative proportion of the methanol conversion or methanol synthesis catalysts should be increased. In this way the final product composition may be manipulated to meet regulatory or other requirements.

DESCRIPTION OF THE PREFERRED EMBODIMENT

Each of the catalyst components of the catalyst mixture used in the process of this invention are well known in the art.

Fischer Tropsch catalysts are those having catalytic activity for converting hydrogen and carbon monoxide reactants into hydrocarbons. Such catalysts are described, for instance in U.S. Pat. Nos. 4,639,431, 4,595,702, 4,361,503 and U.K. Patent 506,064. Such catalysts typically include zinc, iron, cobalt, ruthenium, rhodium or osmium. With the exception of ruthenium, such catalysts typically include chemical and structural promotors such as copper, manganese, chromia, alumina, the alkaline earths, the rare earths and alkali, e.g. carbonates of the Group IA of the periodic table. Particularly preferred FT catalysts for the process of the present invention include iron or cobalt. Potassium is the preferred promotor with iron, to reduce methane production. Potassium promoted iron catalysts are classical known FT catalysts generally recognized as being illustrative of the group of FT catalysts.

Methanol conversion catalysts have catalytic activity for the conversion of oxygenated hydrocarbons such as methanol into hydrocarbons. Such catalysts are typically crystalline aluminosilicate zeolites or crystalline silicates. In particular, the zeolite ZSM-5 is a classical known catalyst illustrative of the group of methanol conversion catalysts. Such catalysts are disclosed, for example, in U.S. Pat. Nos. 4,260,841; 4,269,783; and 4,292,410.

Methanol synthesis catalysts are those having catalytic activity for the watergas shift reaction and the methanol synthesis reaction. Typical examples are oxides of one or more of zinc, copper, iron chromium and aluminum. Particularly preferred are zinc and/or copper methanol synthesis catalysts which may contain chromia and/or alumina. Methanol synthesis catalysts are described in the literature, for instance in U.S. Pat. Nos. 4,292,410 and 4,096,163.

The three catalyst components are utilized in intimate admixture in the process of this invention. The mixture may be used as a powder or slurry, or it may be pelletized prior to or following admixture, as is known in the prior art. Prior to use, the catalyst mixture is preferably reduced to remove a substantial portion of the oxides. Reduction can be accomplished by contacting the catalyst mixture with hydrogen at an elevated temperature and pressure. The temperature should be controlled to avoid substantial agglomeration.

The feedstock to the process is one having a $H_2/CO$ molar ratio greater than 1.9 and preferably at least 2.0. Synthesis gas and reformer gases are exemplary.

The synthesis gas is contacted with the catalyst admixture at elevated pressure and temperature in a pressure reactor. A shell and tube style reactor bed is exemplary of a suitable reactor. Such reactors utilize top down gas flow with heat transfer fluid being circulated around the tubes to remove the heat of reaction. The pressure and temperature conditions are generally mutually dependent and also vary with the particular feedstock and catalysts. While pressures of 50 to 2000 psig are possible, more preferably the pressure will be in the range of 100 to 1000 psig. Temperatures of 200° to 400° C. are possible, the more preferable range being 220° to 360° C. At about 200 psig, a temperature range of about 315°-350° C. is preferred.

At pressures higher than typically used in the art (i.e. greater than 200 psig), the temperature can be dropped below the normal temperature limits in the art (i.e. below 240° C.) with the result that a high quality hydrocarbon product boiling in the gasoline range is produced. At about 500 psig a temperature range of 220°-240° C. is preferred. Below this temperature range, the activity of the iron FT catalyst may drop off, although other catalysts such as a cobalt FT catalyst could operate at a lower temperature.

The process is preferably practiced in a single reactor, that is the feed gases are passed over the three catalysts in intimate admixture in one reactor. Single or multiple fixed beds, or fluidized beds, may be used. Recycle to improve efficiency may be used.

The process is further illustrated by the following non-limiting examples.

EXAMPLES

Catalysts

The following catalysts were used in the examples:

A. FISCHER-TROPSCH CATALYSTS (FT)

CATALYST A1: Promoted iron catalyst G-84B obtained from United Catalysts Inc. United Catalysts Inc. reports the nominal content of G-84B to be $Fe_2O_3$ 88%, $K_2CO_3$ 10% and $Cr_2O_3$ 2%.

CATALYST A2: Promoted iron catalyst C-73 containing $Al_2O_3$ 2-3%, $K_2O$ 0.5-0.8%, and $CaO$ 2-3%, also obtained from United Catalysts Inc.

B. METHANOL CONVERSION CATALYSTS

CATALYSTS B1, B2: ZSM-5 type zeolite was prepared using the method described by Chen et al in U.S. Pat. No. 4,112,056 as modified. ZSM-5 is a synthetic zeolite characterized by parallel straight channels interlocking with zig-zag channels. Two catalysts were prepared with compositions given below. By analysis, the two catalysts had $SiO_2/Al_2O_3$ ratios of 67.6 and 45.2 and the crystal structure was verified by comparison of the x-ray diffraction patterns against standard ZSM-5 obtained from Mobil (below).

| | B1 | B2 |
|---|---|---|
| Si | 42.6 | 36.2 |
| Al | 0.714 | 0.907 |
| Na | 0.234 | 0.680 |
| $SiO_2$ | 91.2 | 77.5 |
| $Al_2O_3$ | 1.35 | 1.72 |
| $Na_2O$ | 0.315 | 0.917 |
| $SiO_2/Al_2O_3$ | 67.6 | 45.2 |

CATALYST B3: Zeolite catalyst silicalite S-115 $SiO_2>99\%$ obtained from Union Carbide Catalysts.

CATALYST B4: ZSM-5 zeolite catalyst obtained from Mobil Research and Development Corporation.

C. METHANOL SYNTHESIS CATALYSTS (MS or WGS)

CATALYST C1: Proprietary Shell Commerical Methanol Synthesis (MS) Catalyst—approximately 40% CuO, 50% ZnO, 10% $Al_2O_3$ with several trace elements. Product designation MS-51-2.

CATALYST C2: MS catalyst C-79 obtained from United Catalysts Inc. This is a low temperature Cu/Zn catalyst.

CATALYST C3: United Catalysts Inc. C61-1 MS Catalyst. United Catalysts Inc. reports the content of C61-1 catalyst to be CuO $33+/-3\%$ by weight, ZnO $65+/-3.0\%$ $Al_2O_3$ 2% maximum, S 0.04% maximum, Na 0.10% maximum, Cl 0.01% maximum. Bulk density $85+/-5$ lbs/cu ft., surface area 30–60 $m^2/g$, pore volume 0.25–0.35 cc/g.

4. INERT FILLER

CATALYST D1; Carborundum.

EXAMPLE 1

EXPERIMENTAL DETAILS

Figure 1:
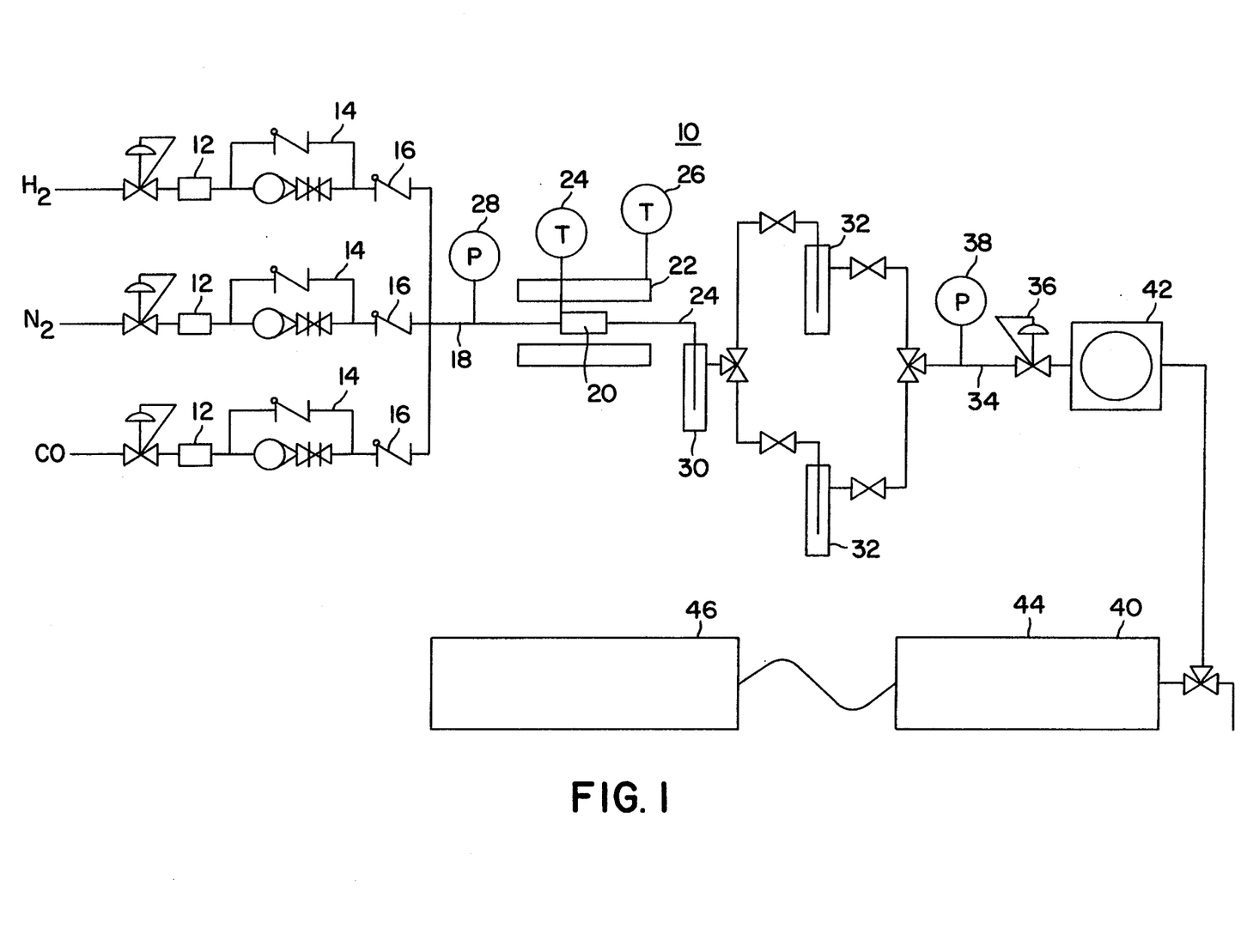
FIG. 1 is a schematic flow diagram of the experimental circuit used in Example 1 to illustrate the process of the present invention.

The flow diagram of the experimental circuit 10 used in this example is shown in FIG. 1. The feed gas streams ($H_2$, $N_2$, CO) were fed through filters 12, mass flow controllers 14 and check valves 16 into line 18. The mass flow controllers were Matheson Model 8100 series. The gas mixture was introduced into the pressurized reactor 20 containing the catalyst or diluent. The reactor 20 was housed in furnace 22. Temperature probes 24, 26 monitored catalyst and furnace temperatures respectively. Inlet pressure to the reactor was monitored by pressure meter 28 in line 18. Products leaving the reactor 20 were passed through a $+15°$ C. trap 30 and two $-75°$ C. traps 32 in the outlet line 34. Pressure was maintained at 200 psig by back pressure regulator 36 in the outlet line 34, as monitored by the pressure meter 38. The outlet gases were fed to a gas chromotograph (GC) 40 through a flowmeter 42. Gases were vented from the GC through vent 44. Data from the GC was analyzed by a data system 46 to measure (a) total hydrocarbon and (b) mixture of hydrocarbons C1 to C3 and $CO_2$. The liquid trapped in trap 30 was analyzed using PONA. PONA is a conventional analytical method for describing the paraffinic, olefinic, napthenic and aromatic components of a predominantly hydrocarbon mixture. Products were also analyzed by GC-MS to separate the components (GC) and then identify the components by mass spectrometry. Gas samples were analyzed throughout each experiment at intervals of 12 minutes.

CATALYST PREPARATION

The G-84B (A1) and MS51-2(C1) catalysts were 14–25 mesh size. The ZSM-5 (B1 and B3) catalysts were fine crystalline powders. In each run, a total of 4 $cm^3$ of catalysts or diluent was loaded into the reactor. The catalyst mixture was pre-treated for each run (to reduce the catalysts) with a flow of $H_2$ at 200° C. and 200 psig for a minimum period of 18 hours. The catalyst combinations and process conditions employed are shown in Table 1 and further described hereinbelow.

EXAMPLE 1(a)

This example illustrates one preferred embodiment of Applicant's invention. Three catalysts were used together—G-84B(A1), ZSM-5(B1), and MS 51-2(C1). All tests were conducted at GHSV 900, and 200 psig at 335° C. The $H_2$/CO ratio of the feed gas was varied. Results in Table 1 show that CO conversion was excellent over $H_2$/CO ratios from 1.5 to 3.0. $C_{5+}$ yield was best for $H_2$/CO=2.5 but was also good at lower ratios. The product slate featured high paraffin content and low aromatic content. For all the tests in Example 1, the oxygenate production was below 2% yield.

EXAMPLE 1(b)

Tests were conducted at $H_2$/CO=2.0 GHSV=900 and pressure=200 psig but at lower and higher temperatures than in example 1(a). At both 290° C. and 380° C. CO conversion was considerably lower, as was $C_{5+}$ yield. The process conditions are further optimized in further examples. The high-temperature test (380° C.) produced high wax levels and the highest aromatic product level (20% of liquid product).

EXAMPLE 1(c)

In this example of the invention, the relative amounts of FT and methanol conversion catalyst were varied, while holding GHSV at 900, pressure at 200 psig and temperature 335° C. A higher level of FT catalyst relative to methanol conversion catalyst gave rise to lower $C_{5+}$ yield.

EXAMPLE 1(d)

In this example the methanol conversion catalyst was changed from a zeolite to silicalite and two ratios with the FT catalyst were tested. Excellent $C_{5+}$ yields were obtained at GHSV 900, pressure 200 psig and temperature 335° C. This example illustrates that product slate can be altered by the choice of methanol conversion catalyst, silicalite produces a high-aromatic hydrocarbon product (16.62%) in comparison with ZSM-5 (12.10%).

EXAMPLE 1(e)

To determine the commercial value of hydrocarbon liquids produced in Example 1, hydrocarbon liquids run from 90-05 (Example 1(a) with ZSM-5) and 91-11 (Example 1(d) with silicalite) were subjected to PONA analysis and octane numbers were calculated. Results in Table 2 show both hydrocarbon liquid products to have a high energy value and excellent utility as a fuel feedstock. The Research Octane Numbers were equal to, or better than, typical light straight run gasoline.

TABLE 1

| PARAMETIC TESTS OF TRIPLE CATALYSTS AT LOW PRESSURE (20 PSIG) | | | | | | | |
|---|---|---|---|---|---|---|---|
| RUN NUMBER | CATALYST VOLUME RATIOS | | | | CATALYST BED TEMPERATURE °C. | FEED GAS VOLUMETRIC RATIO $H_2$/CO | CO CONVERSION % | $C_{5+}$ YIELD |
| | A1 | B3 | B1 | C1 | | | | |
| Example 1(a) | | | | | | | | |
| 90-01 | 1 | 0 | 4 | 5 | 335 | 1.5 | 96 | 21 |

TABLE 1-continued
PARAMETIC TESTS OF TRIPLE CATALYSTS AT LOW PRESSURE (20 PSIG)

| RUN NUMBER | CATALYST VOLUME RATIOS | | | | CATALYST BED TEMPERATURE °C. | FEED GAS VOLUMETRIC RATIO $H_2/CO$ | CO CONVERSION % | $C_{5+}$ YIELD |
|---|---|---|---|---|---|---|---|---|
| | A1 | B3 | B1 | C1 | | | | |
| 90-05 | 1 | 0 | 4 | 5 | 335 | 2 | 93 | 20 |
| 90-02 | 1 | 0 | 4 | 5 | 335 | 2.5 | 96 | 32 |
| 90-03 | 1 | 0 | 4 | 5 | 335 | 3 | 85 | 11 |
| Example 1(b) | | | | | | | | |
| 91-06 | 1 | 0 | 4 | 5 | 290 | 2 | 70 | 9 |
| 91-07 | 1 | 0 | 4 | 5 | 380 | 2 | 80 | 14 |
| Example 1(c) | | | | | | | | |
| 91-08 | 2 | 0 | 3 | 5 | 335 | 2 | 91 | 15 |
| 91-09 | 0.5 | 0 | 4.5 | 5 | 335 | 2 | 88 | 20 |
| Example 1(d) | | | | | | | | |
| 91-10 | 1.00 | 4.00 | 0 | 5 | 335 | 2 | 94 | 20 |
| 91-11 | 0.5 | 3.75 | 0 | 5 | 335 | 2 | 97 | 26 |

TABLE 2
COMPARISON OF CALCULATED OCTANE NUMBERS FOR SAMPLES FROM RUN # 90-05 (WITH ZSM-5) and RUN # 91-11 (WITH SILICALITE)

| | RUN # 90-05 | RUN # 91-11 | LSR GASOLINE | COMMERCIAL GASOLINE |
|---|---|---|---|---|
| Weight % | | | | |
| Paraffins | 47.62 | 40.02 | N.A. | 50(30–86) |
| Olefins | 18.73 | 26.12 | N.A. | 9(0.1–26) |
| Naphthenes | 6.19 | 6.84 | N.A. | 5.5(1.5–10) |
| Aromatics | 12.10 | 16.62 | N.A. | 35(5–55) |
| Oxygenate | 0.19 | 0.0 | N.A. | N.A. |
| Unknowns | 15.16 | 10.4 | N.A. | <1 |
| Octane Numbers (a) | | | | |
| MON | 60.8 | 69.9 | 61.6(b) | 92+ |
| RON | 66.5 | 76.6 | 66.4(b) | 92+ |
| Antiknock Index | 63.6 | 73.3 | 64.0 | 92+ |

(a) Calculated values based on PONA
(b) Typical value far Light Straight Run (LSR) Gasoline

EXAMPLE 2

This example demonstrates the applicability of the process of this invention with the trifunctional catalyst (Run 3.3) in comparison with bifunctional or singular catalyst systems at high pressure, low temperature conditions.

EXPERIMENTAL DETAILS

Figure 2:
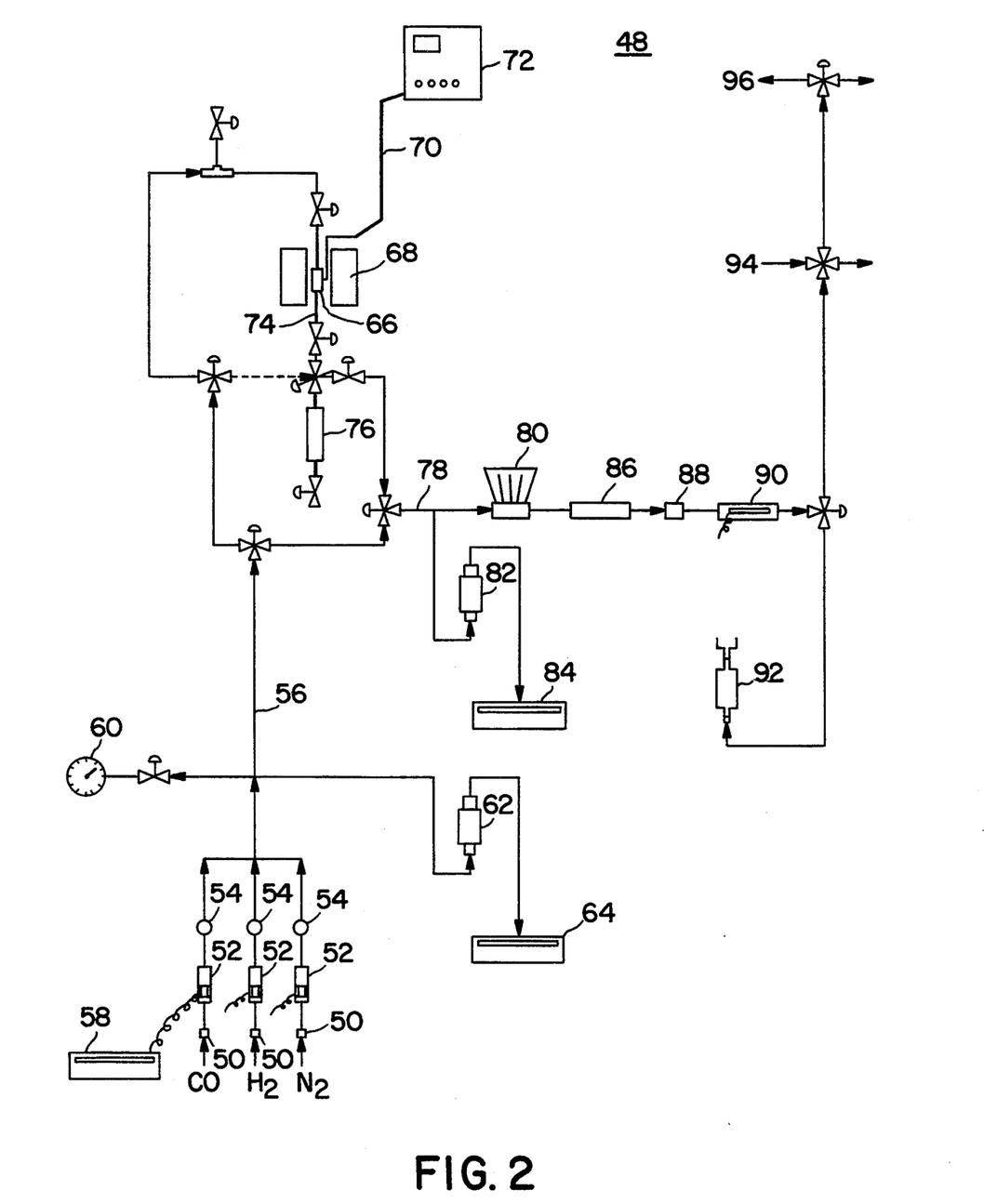
FIG. 2 is a schematic flow diagram of a second experimental circuit used in Example 2 to compare the performance of the trifunctional catalyst of the present invention with bifunctional catalyst mixtures.

The flow diagram of the experimental circuit 48 used in this example is shown in FIG. 2. The feed gas streams of CO, $H_2$ and $N_2$ were fed through pressure filters 50, gas flow controllers 52, and check valves 54 into line 56. The gas flow controllers were connected to a gas blender console 58. The pressure in line 56 was monitored by test gauge 60, pressure transducer 62 and meter 64. The gas mixture was passed vertically downwardly through the catalyst in a reactor 66. The reactor was housed in a clam-shell furnace 68. The temperature in the reactor was monitored by a K type thermocouple 70 and heat controller 72. Liquid product exiting the reactor 66 through line 74 was condensed and collected in vessel 76. Uncondensed gases exiting the reactor passed through the vessel 76 to gas line 78. The reactor pressure was controlled by a back pressure regulator 80, pressure transducer 82 and meter 84 in line 78. The uncondensed gases in line 78 were passed through a molecular sieve trap 86, filter 88, volumetric flowmeter 90 and bubble meter 92. The gases were then passed by a gas exit reduction furnace 94 to a gas chromatograph 96 for analysis. Hydrocarbon liquids trapped in vessel 76 were subjected to PIANO analysis for normal paraffins, iso-paraffins, aromatics, napthenics, and olefins.

As indicated, tests of the trifunctional catalyst admixtures were conducted at lower temperatures and higher pressure than described in Example 1. Operating parameters were fixed as follows: Temperature between 230° C. and 270° C. GHSV 900, pressure 500 psig, $H_2/CO$ ratio 2.0 with a nitrogen tracer. The catalyst mixtures were prepared as set out in Table 3. The catalysts were milled to a narrow mesh size and packed into a vertical reactor of diameter 1-centimeter to a length 10 centimeters and a volume of 7.15 cc. A standard catalyst reduction sequence was followed: temperature was increased at 5° C./min up to 100° C. and 200° C. and 450° C. with a hold time of 1 hour at 100° C. and 200° and hold time of 36 hours at 450° C. The reduction gas was $H_2$.

As shown in Table 4, operating with a high hydrogen ratio relative to CO of 2.0 the trifunctional catalyst ABC provides much higher CO conversion compared with the three bifunctional catalyst combinations, even though those were tested at higher temperatures (250° C.–267° C. versus 231° C. for ABC). Total CO conversion to hydrocarbons was superior with ABC as was the product slate. ABC liquid product was 90% gasoline range with a high proportion of isoparaffins and naphthenes, which provide good octane values, and a low proportion of mono-aromatics, which are toxic materials. Standard Fischer-Tropsch cannot achieve grater than 40–50% selectivity for a given premium product in one step. (New Trends In Coactivation, Ed. L. Guczi, ELSEVIER, 1991, P. 206).

Under the reaction conditions employed, the zeolite catalyst B was not effective alone or in combination with the methanol synthesis catalyst C, providing CO conversion of only 25.6% (Run 4.0), and no hydrocarbons. However, when a small amount of FT catalyst A was included (catalyst type ABC, Run 3.3), CO conversion increased to 91% and hydrocarbon yield was 48.6%. Using the FT catalyst A in a combination with the zeolite catalyst B also give inferior hydrocarbon yield and a low efficiency to gasoline-range products.

Figure 3:
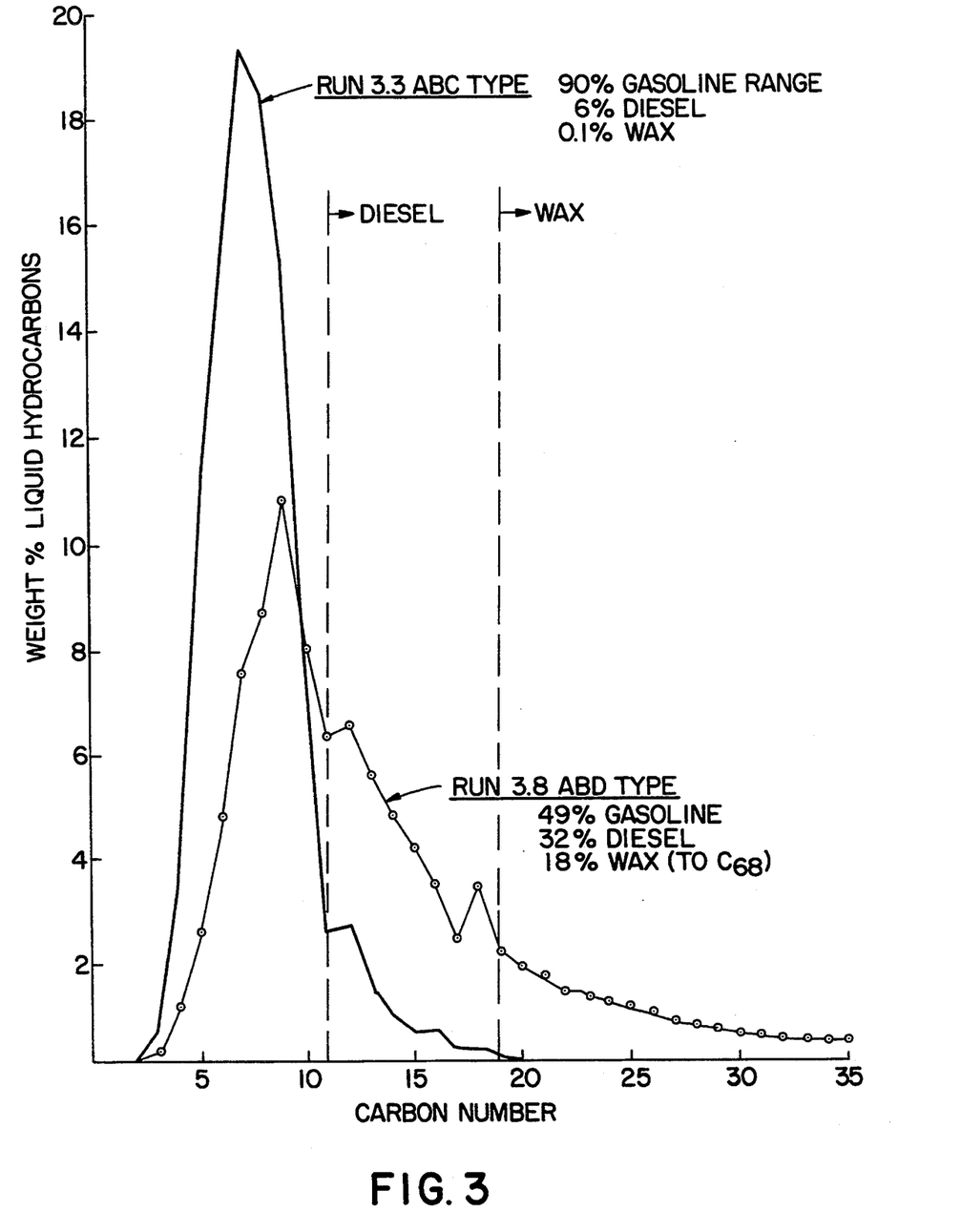
FIG. 3 is a graph plotting the weight percent liquid hydrocarbons against carbon number for the trifunctional catalyst of the present invention (Run 3.3) and a bifunctional catalyst (Run 3.8).

The benefit of Run 3.3, over Run 3.8, the comparative two-part catalyst is shown dramatically in FIG. 3. A hydrocarbon product having a very narrow molecular weight range is produced by the process of this invention at the high pressure, low temperature conditions.

TABLE 3

TRIFUNCTIONAL CATALYST ADMIXTURES[1] USED IN LOW-TEMPERATURE TESTS
EXAMPLE 2

| Run Number | 3.3[2] | 3.8 | 3.9 | 4.0 | 3.4 | 3.7 | 3.5 |
|---|---|---|---|---|---|---|---|
| Catalyst Type | ABC | ABD | ADC | DBC | DDC | DBD | ADD |
| A2, wt ratio | 1.00 | 1.00 | 1.00 | 0 | 0 | 0 | 1.00 |
| B4, wt ratio | 1.50 | 1.60 | 0 | 1.60 | 0 | 1.60 | 0 |
| C2, wt ratio | 4.55 | 0 | 4.55 | 4.55 | 4.55 | 0 | 0 |
| D, wt ratio | 0 | 4.55 | 1.60 | 1.00 | 2.60 | 5.55 | 7.17 |

[1] Total bad volumes were 7.15 cc and length 10 cc. Volume ratios of catalysts were A-type: B-type: C-type, 1:4:5 with inert filler D replacing one of the others in same cases.
[2] Only run 3.3 is in accordance with the process of this patent; all other runs in the table are for purpose of comparison.

TABLE 4

LOW-TEMPERATURE HIGH PRESSURE TEST OF TRIFUNCTIONAL CATALYST (EXAMPLE 2)

| Run Number (see Table 2) | 3.3[1] | 3.8 | 3.9 | 4.0 | 3.4 | 3.7 | 3.5 |
|---|---|---|---|---|---|---|---|
| Catalyst type | ABC | ABD | ADC | DBC | DDC | DBD | ADD |
| Temperature, °C. (furnace) | 231 | 250 | 267 | 258 | 252 | 250 | 250 |
| CO Conversion, % | 91.4[2] | 37.7 | 13.4 | 25.6[3] | 6.8 | | |
| Hydrocarbon Yield % | 48.6 | 27.2 | 0.6 | 0 | 6.7 | * | ** |
| Efficiency: g $C_{5+}$/hr | 0.23 | 0.17 | 0.006 | 0 | 0 | * | ** |
| g $(C_5-C_{11})$/hr | 0.21 | 0.08 | 0.002 | 0 | 0 | * | ** |
| Hydrocarbon Selectivity | | | | | | | |
| $C_3-C_4$ (LPG range) | 4 | 1 | 1 | 0 | *** | * | ** |
| $C_5-C_{11}$ (gasoline range) | 90 | 49 | 40 | 0 | *** | * | ** |
| $C_{12}-C_{19}$ (diesel range) | 6 | 32 | 48 | 0 | *** | * | ** |
| $C_{20+}$ (wax range) | 0.1 | 18 | 11 | 0 | *** | * | |
| $(C_5-C_{11})$ Composition, % | | | | | | | |
| n-paraffins | 18 | 26 | 69 | 0 | *** | * | ** |
| iac-paraffins | 41 | 15 | 19 | 0 | *** | * | ** |
| aromatics | 9 | 11 | 4 | 0 | *** | * | ** |
| naphthenes | 18 | 9 | 6 | 0 | *** | * | ** |
| olefins | 14 | 39 | 2 | 0 | *** | * | ** |
| benzene | 0.1 | 0.4 | 0.2 | 0 | *** | * | ** |
| toluene | 0.3 | 0.8 | 0.5 | 0 | *** | * | ** |
| Mass balances, % | | | | | | | |
| total | 104 | 102 | 101 | 100 | 101 | * | ** |
| carbon | 100 | 104 | 100 | 933 | 100 | | |
| hydrogen | 102 | 102 | 98 | 100 | | | |
| oxygen | 101 | 104 | 105 | 104 | 100 | | |
| Analysis period, hrs | 74–144 | 91–165 | 0–136 | 0–142 | 0–49 | 0–24 | 66 |

[1] Only Run 3.3 Is In accrodance with the process of this patent: the other runs are for comparison purposes.
[2] Co conversion activity loss was 3.1 vol %/100 h.
[3] Product was mainly methanol and dimethyl after.
[4] Product was 99% methanol
*No Activity.
**Activity Negligible.
***No hydrocarbons produced in these ranges.

This example demonstrates a very strong and unexpected synergy when the trifunctional catalyst ABC is used under conditions of high hydrogen feed gas ratios of approximately 2.0 or greater, which ratios have never been tested before. Prior art would have predicted extremely high $CO_2$ yields whereas the yields observed were only those typical of FT catalysts and benefits occurred in total hydrocarbon yield, hydrocarbon $C_{5+}$ (liquids) yields, gasoline range hydrocarbon selectively and a superior liquid product slate with high energy value and low toxicity.

Table 5 shows the superiority of Run 3.3 to both the commercial SASOL FT-process and the Mobil Methanol-to-gasoline (MTG) process, since Run 3.3, provided a narrower product distribution centred on gasoline, the most valuable commodity. Furthermore Run 3.3, was a direct conversion of syngas to hydrocarbon, whereas the MTG process requires the manufacture of the intermediate compound methanol as feedstock.

TABLE 5

| | Distribution of $C_3-C_{19+}$ products | | |
|---|---|---|---|
| | SASOL[3,4] FIXED BED | RUN 3.3[1] | MOBIL[2,3,4] (ZSM-5) |
| LPG $C_3$, $C_4$ | 11 | 4 | 18 |
| Gasoline $C_5-C_{12}$ | 25 | 90 | 82 |
| Diesel $C_{13}-C_{18}$ | 17 | 6 | 0 |
| Heavy Oil $C_{19+}$ | 47 | 0.1 | 0 |
| Aromatics, | 0 | 9 | 39 |

TABLE 5-continued

| Distribution of $C_3$-$C_{19+}$ products | | |
|---|---|---|
| SASOL[3,4] FIXED BED | RUN 3.3[1] | MOBIL[2,3,4] (ZSM-5) |
| % of gasoline | | |

[1]Only the data from Run 3.3 is in accordance with the present invention.
[2]Product from methanol feed to ASM-5 zeolite
[3]Iron Fischer-Tropsch catalyst
[4]Source - From Encyclopedia of Chemical Technology, Edited by Kirk-Othmer, Third Edition, Volume 5, p. 46. Interscience Publishers, New York, N.Y.

EXAMPLE 3

This example is included to compare the trifunctional catalyst processes of this invention with a bifunctional catalyst process such as taught by Dwyer.

The trifunctional catalyst admixture test was conducted with a high $H_2/CO$ ratio of 2.0 obtained from a natural gas reforming (Run 06). For comparison purposes, the methanol synthesis catalyst mixtures was left out in a comparison test, run 05. The catalyst mixtures, as set out in Table 6, were reduced over 30-hour periods with hydrogen while controlling the reduction temperature below 300° C. Catalyst bed size was 4 cc and the tests were operated in a horizontal mode. An internal thermocouple was used to measure catalyst bed temperature. Pressure was 200 psig and the gas hourly space velocity was 900.

Reformer gas derived from natural gas feedstock already contains abundant hydrogens (i.e. $H_2/CO$ molar ratio of 2.0 of greater). Promoting the further increase in hydrogen and reduction in CO would be highly counter-productive. Nevertheless, a test of these ideas was conducted, with surprising and counterintuitive results. The prior art teaches that the inclusion of a methanol synthesis catalyst, as in Run 06, would increase CO selectivity to $CO_2$ by the watergas shift reaction causing a reduction in hydrocarbon yield in comparison with the same catalyst system not containing the WGS catalyst (Run 05). However, the results were contrary to expectations. The trifunctional catalyst admixture (ABC) (Run 06) containing the WGS catalyst (C-type) gave superior CO conversion, hydrocarbon yield and lower $CO_2$ selectivity in comparison with the bifunctional catalyst (ABD) of Run 05 (Table 7).

TABLE 6

| Catalysts used in Example 3 | | |
|---|---|---|
| Run Number | 06 | 05 |
| Catalyst Type | ABC | ABD |
| A1, wt ratio | 1.00 | 1.00 |
| B2, wt ratio | 1.89 | 1.89 |
| C3, wt ratio | 5.64 | 0 |
| D, wt ratio | 0 | 4.09 |

Total bed voluem was 4 cc. Volume ratios of catalysts were A-type: B-type: C-type, 1:4:5 with inert filler D replacing the C-type catalyst in Run 06.

TABLE 7[1]

| (Example 3) | | |
|---|---|---|
| Run Number | 06 | 05 |
| Catalyst type | ABC | ABD |
| Temperature furnace °C. | 313 | 326 |
| Temperature Catalyst °C. | 334 | 336 |
| Temperature differential °C. | 19 | 10 |
| CO Conversion % | 90 | 61 |
| Hydrocarbon yield % | 58 | 37 |
| $C_{5+}$ yield | 39 | 23 |
| Selectivities | | |
| $CO_2$ | 36 | 41 |
| $C_1 + C_2$ (gases) | 9 | 11 |
| $C_3 + C_4$ (LPG range) | 11 | 12 |
| $C_{5+}$ | 44 | 36 |
| ($C_5$-$C_{11}$) Composition, % | | |
| n-paraffins | 44 | 11 |
| iso-paraffins | 24 | 22 |
| Aromatics | 9 | 14 |
| Naphthenes | 7 | 9 |
| Olefins | 16 | 44 |
| Mono-aromatics | 1.6 | 2.7 |

[1]Operating Conditions: GHSV = 900, inlet pressure 200 psi, $H_2/CO$ ration 2.0. See Table 5 for the catalyst compositions.
[2]Run 05 is similar to the process of Dwyer et al for comparison purposes.

The entire disclosures of all applications, patents and publications, cited above and below, are hereby incorporated by reference. Also incorporated by reference is applicants' Patent application Ser. No. 07/606,755, filed Oct. 31, 1990, and the continuation application thereof, being Ser. No. 07/795,153, filed Nov. 20, 1991, of which this application is a continuation-in-part.

The embodiments of the invention in which an exclusive property or privilege is claimed are defined as follows:

1. A catalytic process for the production of a hydrocarbon mixture having a higher percentage of paraffinic and olefinic hydrocarbons than aromatic hydrocarbons, comprising:
    providing a gas mixture of hydrogen and carbon monoxide having a molar ratio of hydrogen to carbon monoxide which is greater than about 1.9;
    reacting the gas mixture at elevated pressure and temperature in contact with a trifunctional catalyst mixture consisting essentially of a first Fischer-Tropsch catalyst having catalytic activity for converting hydrogen and carbon monoxide reactants into hydrocarbons, a second catalyst having catalytic activity for the conversion of methanol into hydrocarbons, and a third catalyst having catalytic activity for the water-gas shift reaction and the methanol synthesis reaction;
    to produce a hydrocarbon mixture boiling in the gasoline and diesel range, said trifunctional catalyst having a relative proportion of said first catalyst to said second and third catalysts effective to provide said hydrocarbon mixture having a higher percentage of paraffinic and olefinic hydrocarbons than aromatic hydrocarbons.

2. The process as set forth in claim 1, in which the process is conducted in a single reactor, and wherein the components of the trifunctional catalyst are in intimate admixture.

3. The process as set forth in claim 1, wherein the Fischer-Tropsch catalyst is an iron or cobalt catalyst.

4. The process as set forth in claim 3, wherein the Fischer-Tropsch catalyst is a potassium-promoted fused iron oxide catalyst.

5. The process as set forth in claim 3, wherein the methanol conversion catalyst is a crystalline aluminosilicate or a crystalline silicate.

6. The process as set forth in claim 5, wherein the methanol conversion catalyst is a synthetic crystalline zeolite ZSM-5 or silicalite catalyst.

7. The process as set forth in claim 5, wherein the water gas shift and methanol synthesis catalyst is an oxide of one or more of (i) zinc and (ii) copper.

8. The process as set forth in claim 7, wherein the water gas shift and methanol synthesis catalyst is a Cu- Zn-O catalyst which is reduced to remove a substantial portion of the oxides.

9. The process as set forth in claim 7 in which the molar ratio of hydrogen to carbon monoxide is at least 2.0 and less than 3.

10. The process as set forth in claim 7 in which the molar ratio of hydrogen to carbon monoxide is at least 2.0 and less than 2.5.

11. The process as set forth in claim 7 in which the reaction is conducted at a temperature in the range of 200° to 400° C. and at a pressure greater than 200 psig.

12. The process as set forth in claim 7 in which the reaction is conducted at a temperature in the range of 220° to 360° C. and at a pressure greater than 200 psig.

13. The process as set forth in claim 7 in which the reaction is conducted at a temperature in the range 200° to 240° C. and at a pressure greater than 500 psig.

* * * * *